United States Patent [19]

Goldberg et al.

[11] Patent Number: 5,601,580
[45] Date of Patent: Feb. 11, 1997

[54] VENOUS VALVE CUTTER

[75] Inventors: Mark C. Goldberg, Boston, Mass.;
Alexander Poloyko, Morton Grove, Ill.

[73] Assignee: Uresil Corporation, Skokie, Ill.

[21] Appl. No.: 313,229

[22] PCT Filed: Apr. 9, 1993

[86] PCT No.: PCT/US93/03358

§ 371 Date: Jan. 9, 1995

§ 102(e) Date: Jan. 9, 1995

[87] PCT Pub. No.: WO93/20764

PCT Pub. Date: Oct. 28, 1993

Related U.S. Application Data

[63] Continuation-in-part of Ser. No. 865,850, Apr. 4, 1992, Pat. No. 5,304,189.

[51] Int. Cl.[6] .................................................. A61B 17/32
[52] U.S. Cl. ............................................................. 606/159
[58] Field of Search .................................. 606/159, 167, 606/170, 179, 194; 604/22

[56] References Cited

U.S. PATENT DOCUMENTS

| | | |
|---|---|---|
| 3,837,345 | 9/1974 | Matar . |
| 4,493,321 | 1/1985 | Leather . |
| 5,026,383 | 6/1991 | Nobles ................................ 606/159 |
| 5,047,041 | 9/1991 | Samuels ............................. 606/159 |

FOREIGN PATENT DOCUMENTS

| | | | |
|---|---|---|---|
| 3717926 | 12/1988 | Germany ............................ 606/159 |
| 0537676 | 12/1976 | U.S.S.R. ............................. 606/159 |

OTHER PUBLICATIONS

American V. Mueller The Surgical Armamentarium p. 98 (1980).

*Primary Examiner*—Michael Powell Buiz
*Assistant Examiner*—Patrick W. Rasche
*Attorney, Agent, or Firm*—Laff, Whitesel, Conte & Saret, Ltd.

[57] ABSTRACT

An improved valve cutter for in-situ incision of valve leaflets which safely, efficiently, and consistently renders venous valves incompetent while minimizing frictional forces on the endothelium of the vessel and preventing inadvertent contact between cutting surfaces and the intima of the vein wall. The valve cutter includes a plurality of proximally directed prongs presenting sharp edges, where the prongs are separated by slots similarly presenting sharp edges to pierce the valve leaflets so that the cutting head is provided with a continuous cutting surface in multiple planes running along the entire forward edge of the cutting head. Fiber optics provided for viewing the valves as they are penetrated by the sharp cutting edges.

5 Claims, 4 Drawing Sheets

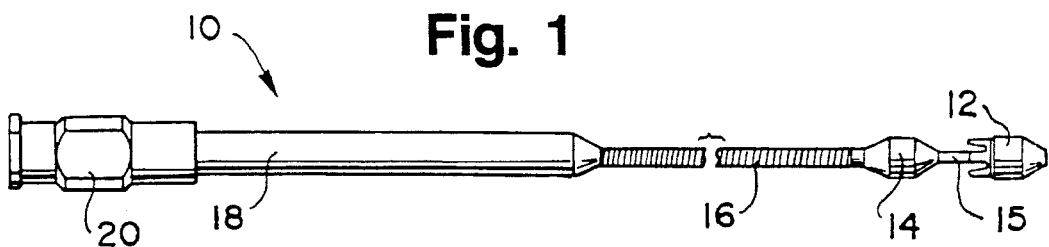
Fig. 1
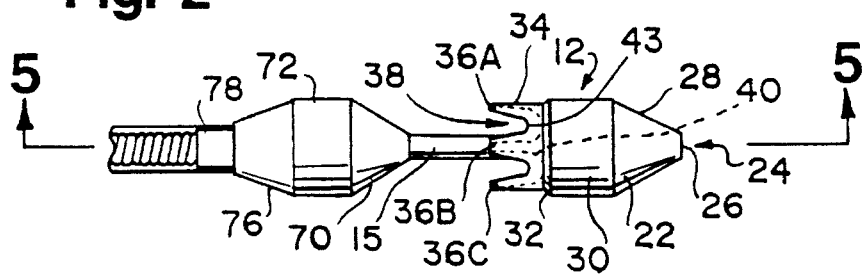
Fig. 2
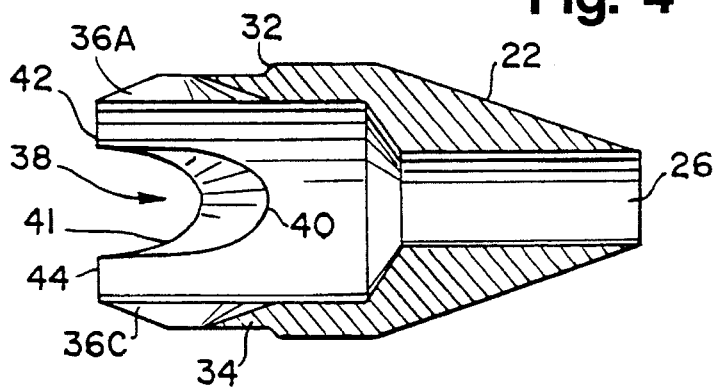
Fig. 4
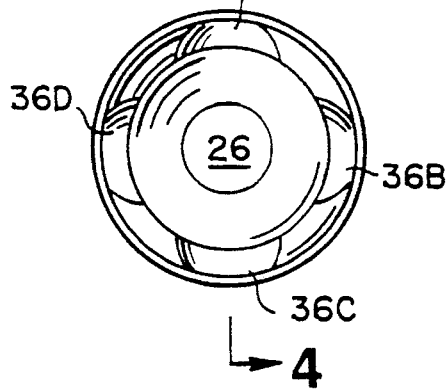
Fig. 3
Fig. 3A

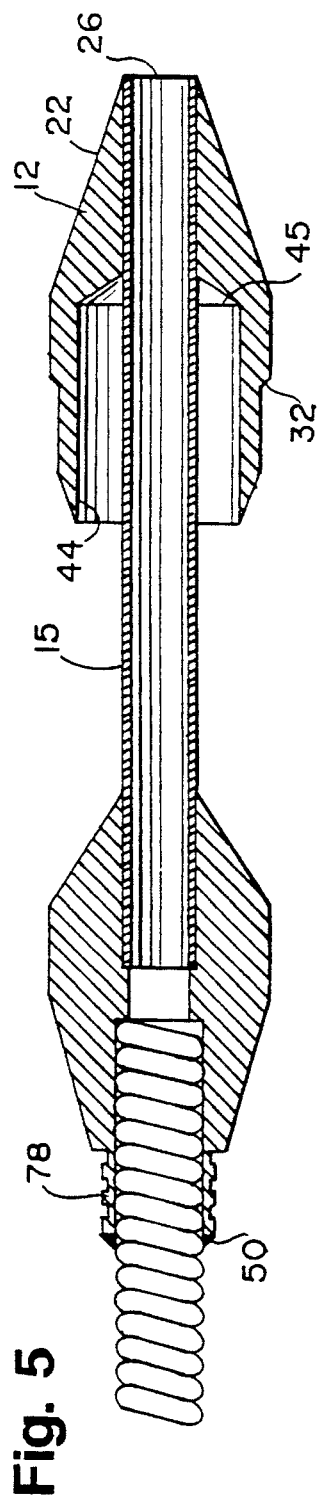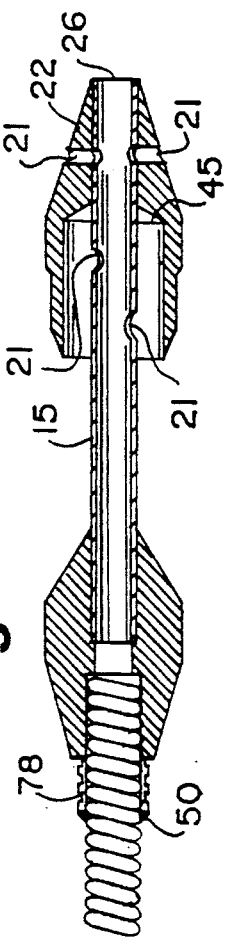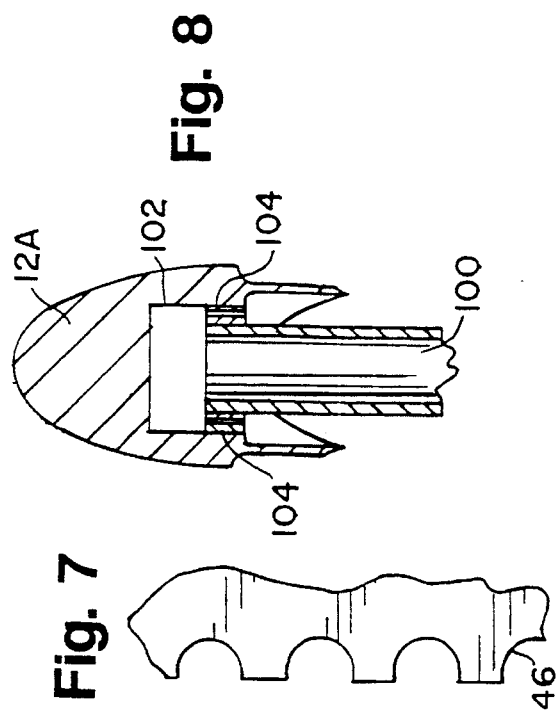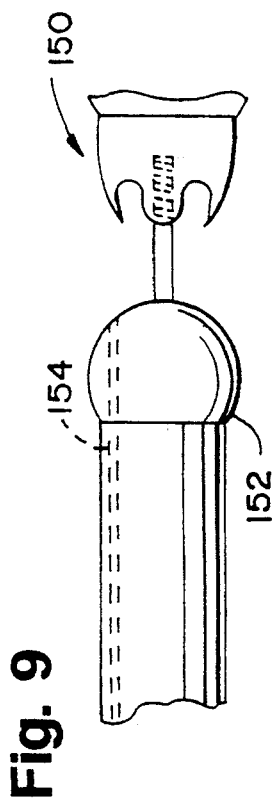

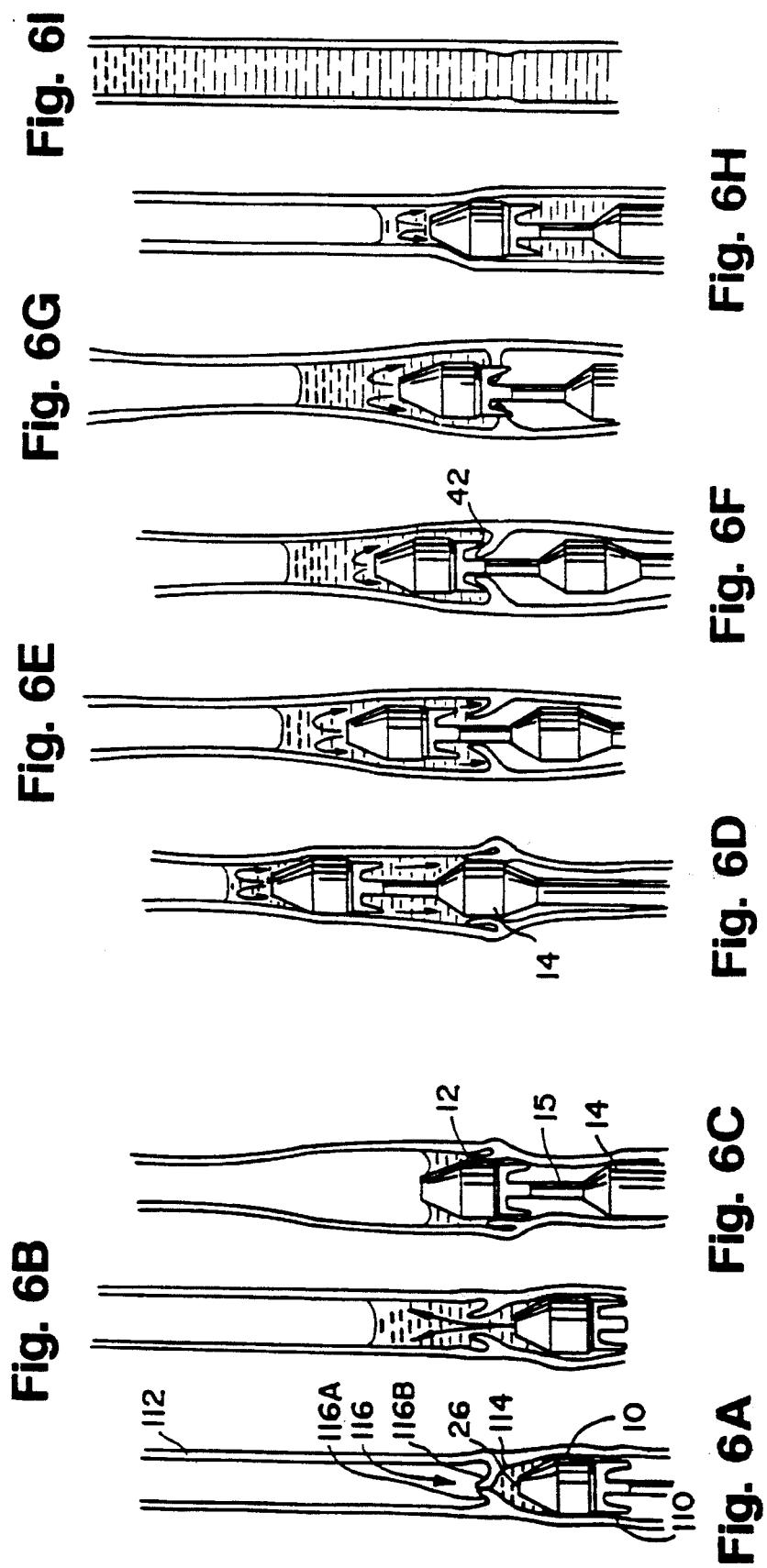

VENOUS VALVE CUTTER

This is a 371 CPU/US93/03358 filed on Apr. 4, 1993 which is a continuation-in-part of U.S. patent application Ser. No. 07/865,850 filed Apr. 4, 1992 now U.S. Pat. No. 5,304,189.

BACKGROUND OF THE INVENTION

This invention is directed generally to rendering venous valve leaflets incompetent for in-situ arterial bypass in patients requiring arterial reconstruction for chronic limb-threatening ischemia. More particularly, this invention is directed to a venous valve cutter having unique improved cutting surfaces to facilitate the incision of the leaflets and a unique irrigation system to minimize frictional forces on the endothelium of the vein when introducing and withdrawing the cutter.

A common form of chronic limb-threatening ischemia, femorotibial, obstructive disease, typically is treated by using the greater saphenous vein as a bypass conduit. Traditionally, this vein has been removed from its anatomic bed and reversed to overcome the obstruction to flow from its one-way valves. The distal end of the "reversed flow" greater saphenous vein is then grafted to the femoral artery and its proximal end is grafted to the outflow artery beyond the obstruction.

There are a number of problems inherent in the use of a reversed flow saphenous vein as a bypass conduit. The narrow distal end of the vein may not permit enough arterial in-flow from its new parent vessel, whereas the wide proximal end of the vein makes an anastomosis to the 2–3 millimeter distal outflow vessel cumbersome. Also, the body of the vein may twist or compress and be damaged during the vein removal, reversal and replacement process and it is difficult to preserve the very sensitive endothelial layer of the vein during the removal and replacement process. Furthermore, the process may impair the blood vessel's blood supply (the vasa vasorum).

Bypass procedures in which a vein is used as it lies anatomically within the body, without removal, reversal and replacement, i.e., "in-situ situ vein bypasses", generally overcome most problems associated with removing, reversing and replacing the vein. This is most commonly accomplished in treating femorotibial disease by moving a valve cutter through the saphenous vein to incise the venous valve leaflets.

Since Carrel and Guthrie's publication of the techniques required for a small vessel anastomosis, vascular surgeons have attempted infrainguinal distal revascularizations. The advantage of the in-situ technique for saphenous vein bypass are first that the narrow end is anastomosed to the smaller artery distally with the graft tapering in the appropriate direction. This improves the hemodynamics at both anastomoses. A second consideration is that the adventitial blood supply to the vein is preserved to help protect the endothelial lining of the vein.

Typically, in performing this procedure either the distal end of the vein is anastomosed to the femoral artery to allow arterial blood to pass into the vein or a saline solution is pumped through a cannula into the vein to provide the required pressure to distend the vessel and close the valves. These procedures are performed to ensure that the valve cutter will meet and incise the valve leaflets in their closed, extended position. Once all of the valves are made incompetent, the vein becomes suitable for use as an arterial bypass conduit.

Unfortunately, it is quite difficult using currently available valve cutters, to efficiently and consistently incise and render the valves incompetent without damaging the endothelium of the vein or even piercing the vein wall. The various currently available valve cutter devices are difficult to manipulate, often do not center and catch the valve leaves properly, and can cause significant damage to the vein due to intimal contact between the surfaces of the cutting head and the vein wall and tearing at the points of valve attachment to the vessel wall.

U.S. Pat. No. 3,837,345, entitled "Venous Valve Snipper", describes a device for incising valves in vein grafts to bypass blocked arteries. This device is not intended to be used in-situ. The instrument has a closed position and an open position: it is maneuvered past the venous valves in the direction of blood flow, opened and withdrawn whereby sharp spikes spear and impale the venous valve leaflets which are then hopefully incised by closing the device in a scissors-like motion.

U.S. Pat. No. 4,493,321, entitled "Venous Valve Cutter for the Incision of Valve Leaflets In-situ", describes a valve cutter in the shape of a reverse arrowhead for preparing a vein in-situ for an arterial bypass. The valve cutter includes a rounded leader, a cutting blade enclosed in a protective support, a torsionally rigid rod connecting the leader to the cutting blade, and a catheter attached to the cutting blade support with suture material. The valve cutter is used by making proximal and distal incisions in the vein, passing a rod through the vein, attaching the valve cutter and pulling it down the vein while introducing fluid through the attached catheter to close the valves before incising them, and then returning the valve cutter assembly to the proximal incision. The orientation of this device must be continuously controlled to prevent the cutting blade from catching and tearing the orifice wall of a contributing venous branch and to ensure engagement and incision of both leaflets of each valve.

U.S. Pat. No. 5,047,041, entitled "Surgical Apparatus for the Excision of Vein Valves In-situ", describes a valve cutter in which a circular cutting head affixed to a cable is preceded by a dilating segment also affixed to the cable. The circular cutting edge has series of rounded guide teeth which are intended to guide the valve leaflets into cutting grooves which are supposed to engage and then cut the valve leaflets. Unfortunately, the rounded unsharpened guide teeth pull, stretch and likely irregularly tear the valve leaflets before any cutting can begin.

SUMMARY OF THE INVENTION

Accordingly, this invention is directed to an improved venous valve cutter for in-situ incision of valve leaflets which safely, efficiently, and consistently renders the venous valves incompetent while minimizing frictional forces on the endothelium of the vessel and preventing inadvertent contact between cutting surfaces and the intima of the vein wall.

An important object of this invention is the provision of a venous valve cutter for in-situ incision of valve leaflets which does not pull, stretch or tear the leaflets' attachments to the vessel wall.

Another important object of this invention is the rendering of the venous valves incompetent for in-situ arterial bypass by cutting blades which engage and penetrate the valve leaflets immediately on contact with the cutting head.

A further object of this invention is the provision of a venous valve cutter with interchangeable cutting heads which enable the surgeon to appropriately match the head size to a vessel's tapering lumen.

Yet another object of this invention is the provision of an integral venous valve cutter irrigation system which helps center the device while irrigating and opening the valves and distending the lumen of the vessel to prevent contact with the vessel wall as the device is passed up through the vessel in preparation for the valve cutting procedure.

Still another object of this invention is the provision of a valve cutter with an irrigation system in which fluid is allowed to pass retrograde into the cutter head of the device to flush and lubricate its cutting surfaces.

Yet a further object of the invention is to provide a venous valve cutter having a cutting head with a cylindrical portion which helps center the cutter in the vein.

Yet another object of the invention is to provide a venous valve cutter having a cutting head with a cylindrical portion in which channels are provided to facilitate fluid passage in tightly fitting vessels.

The improved venous valve cutter of the present invention includes, as a key feature, a cutter head having a plurality of generally proximally directed prongs separated by slots, where the prongs have flat forward cutting edges and the slots also have cutting edges along their entire length so that the prongs first pierce the valve leaflets whereupon the cutting surfaces of the slots continue the shearing action as the cutter moves through the valve. The present invention further includes a unique irrigation system for valve cutters in which saline or other fluid passes through the cutter head as the cutter moves through the vessel, first to minimize trauma as the cutter is passed through the vessel and the valves and then to minimize trauma and enhance the effectiveness of the shearing action as the valve leaflets are cut.

BRIEF DESCRIPTION OF THE FIGURES

The features of the present invention which are believed to be novel are set forth with particularity in the appended claims. The invention, together with further objects and advantages thereof, may best be understood by reference to the following description taken in connection with the accompanying drawings in which:

FIG. 1 is a front plan view of a horizontally disposed, improved venous valve cutter in accordance with the present invention;

FIG. 2 is an enlarged view of the cutter head and leader of the valve cutter of FIG. 1;

FIG. 3 is an enlarged end view, in elevation, of the cutter head of FIG. 1, viewing the cutter head from the pronged end;

FIG. 3A is a modified enlarged end view, in elevation, of the cutter head of FIG. 1, viewing the cutter head from the pronged end in which channels are provided to facilitate fluid passage in tightly fitting vessels;

FIG. 4 is an enlarged elevation view of the cutter head of FIG. 1, shown in section, taken along lines 4—4 of FIG. 3;

FIGS. 4C and 4D are elevation views of an alternative unitary interchangeable valve cutter head and leader design and FIG. 4E is an elevation view of alternate catheter design which may be fitted to the valve cutter head and leader of FIGS. 4C and 4D as well as that of FIG. 9 below;

FIG. 5 is an enlarged view of the cutter and leader assembly portion of the device of FIG. 1, shown in section, taken along lines 5—5 of FIG. 2;

FIG. 5A is an enlarged view of the cutter and leader assembly portion of the device of FIG. 1, shown in section, taken along lines 5—5 of FIG. 2 in which optional irrigation ports are formed in the cutter head and in the cutter stem.

FIGS. 6A–6I comprise a diagrammatic representation of the operation of the valve cutter of FIG. 1;

FIG. 7 is a planar representation of the continuous cutting surface of the present invention;

FIG. 8 is an enlarged front plan view, shown in section, of a cutter head in accordance with the present invention, in which provision is made for back flushing the cutter head as the valve leaflets are excised; and FIG. 9 is an enlarged partial view of an alternative embodiment of the improved venous valve cutter of the present invention in which a fiber optic element is provided for viewing the vessel and the action of the cutting head in rendering the valves incompetent, and for assessing the effectiveness of the cut.

DESCRIPTION OF THE PREFERRED EMBODIMENT

Figure 4A:
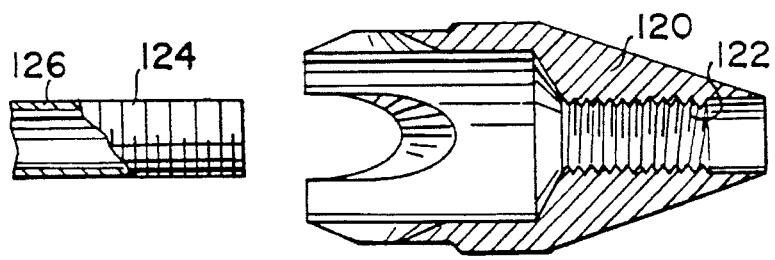
FIG. 4A is a schematic representation of a interchangeable valve cutter head.

An improved venous valve cutter or valvulotome in accordance with the present invention is generally designated in FIG. 1 by the numeral 10. Although the valve cutter is discussed below in connection with in-situ bypass procedures, it is not limited to this and may be applied to any vascular operation requiring a non-reversed vein graft. Such applications may, for example, be found during distal infrainguinal bypasses when a non-anatomic position is required (ex: profunda femoris to anterior tibial artery), composite vein infrainguinal bypasses, or even an aorta-renal bypass.

Valve cutter 10 comprises a cutter head 12, a leader 14, a stem 15 between the cutter head and the leader, a catheter 16, a handle 18 and a combination hub and injection port 20.

Cutting head 12 may be made of any material which is safe for use in the body and is capable of taking and holding a knife edge. Stainless steel is preferred for the fabrication of the cutting head. The valve cutter may, for example, include 1.5 mm, 2.4 mm, 3.0 mm, and 4.0 mm or other size diameter cutting heads. The choice of cutter head size is a matter of judgement although it is recommended that a size smaller than the vein be employed.

Turning now to FIG. 2, an enlarged view of cutter 12 joined to leader 14 by stem 15 is shown. The distal end of cutter 12 is in the shape of a cone 22 truncated and bored at its distal tip 24 to provide an irrigation port 26 which communicates with a central lumen 27 (FIGS. 4 and 5). The edge 28 of irrigation port 26 preferably is rounded in order to minimize the danger of intimal damage.

Immediately proximal to cone 22, the cutter head surface flows smoothly into a first cylindrical section 30 which is undercut along its circumference at 32 to form a second cylindrical section 34 of slightly lesser outer diameter than the first cylindrical section. This undercut further minimizes the danger of damage to the vein wall as the cutter moves past the valves.

A plurality of proximally directed prongs 36 are at the proximal or "business end" of cylindrical section 34. At least two prongs are required, although four prongs, 36A, 36B, 36C and 36D are depicted in the illustrated preferred embodiment, and more can be used. The prongs are defined by half-oval slots 38 in cylindrical section 34.

The inside edges of prongs 36A–36D, as defined by slots 38, are bevelled back to a margin 40 and ground to present sharp cutting surfaces 41, as best seen in FIG. 4. Additionally, the flat leading edges 42 of the prongs are ground on their inner surfaces at 44 to similarly present sharp cutting edges. Thus, cutting head 12 is provided with a continuous cutting surface in multiple planes running along the entire forward edge 46 of the cutting head, which is shown in FIG. 7 as if the wall of the cutter were laid out in a plane. As a result, flat leading edges 42 of the prongs pierce the leaflets whereupon the eight sharp cutting surfaces 41 continue the shear of the venous valves as the cutter is pulled through to gently widen the cut in the valve until the apices 43 of the slots are reached whereupon the entire valve can be cleanly cored out and captured in the cutter head at 45 (FIG. 5).

The use of leader 14 is preferred but not required in the practice of the invention. Leader 14 is attached to cutter head 12 through a rigid stem 15, which is centered on the axis of both the cutter and the leader and forms an open lumen from irrigation port 26 through the distal end 50 of the leader, as seen in FIG. 5. Also, a rigid spring may be used as stem 15 to provide an additional irrigation site through the spacings between the coils of the spring. Finally, stem 15 must be of a length sufficient to permit the valve leaflets to close (clear the leader) before meeting the leading edges 42 of prongs 38A–38D.

Leader 14 includes a conical surface 70 which flows into a cylindrical surface 72 and then a trailing conical surface 76. A nipple 78 is provided at the proximal end of the leader for attachment to catheter 16.

In an alternate embodiment, catheter 16 comprises a tightly wound coil spring covered with an inextensible sheath. The coil spring is preferably stainless steel and the sheath is preferably a low surface friction thromboresistant material such as polyurethane. This sheathed coil structure is conformable, compliant and flexible yet has longitudinal rigidity for better centering.

Catheter 16 is attached to plastic handle 18 which may be made of polyurethane or other suitable materials. The surgeon will grip this handle as the device is passed through the vein, and may rotate the cutter head, if desired. However, even without physically rotating the device, the advancing cutting edges of the prongs produce incisions that advance about the valve leaflets in a circumvolutory fashion.

The hub/injection port 20 is attached to a source of saline (not shown). The saline or other fluid flows from the irrigation port distending the vessel's lumen and aiding in the centering of the device while irrigating and opening the valves as the valve cutter is passed up through the vessel in preparation for the valve cutting procedure. This minimizes trauma to the vessel wall, to preserve a viable, untraumatized and hence non-thrombogenic endothelium. In an alternative embodiment, depicted in FIG. 5A, irrigation ports 21 could be formed in cone 22 or in stem 15 to either enhance the effect of the irrigation from irrigation port 26 or to replace port 26 which could be capped off.

The present valve cutter adds a particular advantage over other such devices if the proximal anastomosis is not performed prior to rendering the valves incompetent since this permits the valve cutter to ensure that the valves are closed and thus the valves' maximum surface area is exposed for the cutting blade to engage the valves.

Further, the present valve cutter allows, with a small fiber optic bundle inserted through the irrigation channel in the valve cutter, direct observation of the incised valves. In an alternate embodiment, as illustrated in FIG. 9, a fiber optic bundle 154 is mounted in the leader 14 of the valve cutter to enable the surgeon to view and monitor the action of the cutting surfaces as they render each successive valve incompetent.

In yet another embodiment of the invention, underside irrigation is used in a valve cutter 12A as depicted in FIG. 8. In this embodiment, saline or other fluid is passed through the catheter 100 and into the rearward section 102 of the cutting head. The saline accumulates at 102 and is forced out through ports 104 to flush and lubricate the cutting edges of the cutting head as they cut into the valve leaflets.

Turning now to FIGS. 6A–6I, valve cutter 10 is introduced through the proximal end 110 of vein 112 and heparinized saline 114 is irrigated through port 26 in the cutting head of the valve cutter to dilate and lubricate vein 112 before the advancing cutting head which is shown passing up through valve 116, comprising leaflets 116A and 116B, in FIGS. 6B and 6C. The pressure gradient established through irrigation port 26 opens the valve leaflets ahead of the advancing valve cutter (FIG. 6B) which then passes through the valve as shown in FIG. 6C, well lubricated by the saline front advancing ahead of it.

When the cutting head of the valve cutter has cleared the valves, its direction is reversed (FIGS. 6D–6H). The valve cutter is thus positioned at the most proximal aspect of the vein and gently the hydrostatic pressure is re-established to close the nearest proximal valve. The irrigation pressure gradient should be gentle to prevent or minimize hydrostatic pressure injuries as the valve cutter is gently advanced, with the vein distended, allowing it to float proximally. The hydrostatic pressure is maintained so that, with the leaflets closed, leading edges 42 of the cutting head prongs engage the leaflets near the vein wall and immediately pierce them forming a small incision which is gently widened by the curved cutting surfaces 41 (FIGS. 6F–6H) until the valve is rendered incompetent leaving a clean and minimally damaged former valve site, as seen in FIG. 6I. The irrigation during the process is provided at a level sufficient to help center the device while minimizing the danger of hydrostatic pressure injuries to the vein.

The valve cutter 10 is then positioned at the most distal aspect of the next valve and gently the hydrostatic pressure is re-established to close that valve which is engaged and gently incised out as described above. Hydrostatic pressure is maintained and the valve cutter is pulled down, sequentially engaging and cutting the next distal valve until all the valves have been rendered incompetent.

If the surgeon wishes to construct a proximal anastomosis prior to using the valve cutter, thereby allowing the systemic arterial pressure to close the valves, the irrigation port may be capped off to prevent loss of blood. However, the proximal anastomosis does not negate the advantage of irrigation during the initial introduction of the valve cutter at the distal end of the vein. Also, the surgeon may wish to pass a fiber optic bundle through the irritation channel to view the cutting of the valves as the valve cutter proceeds down the vein.

In an alternative embodiment of the invention, as illustrated in FIG. 3A, channels 110–110D are provided in the cylindrical portion 30 of the cutter head to permit fluid flow when the cutter head encounters a tightly fitting portion of a vessel thereby preventing undesirable pressure build up and ensuring continued lubrication as the cutter passes through the snugly fitting portion of the vessel.

In yet another alternate embodiment of the invention, a series of differently sized cutter heads are provided in a kit with a single valve cutter assembly. This embodiment of the invention is depicted in FIG. 4A by a representative interchangeable cutter head 120 which has an inner female threaded portion 122 dimensioned to screw onto a corresponding male threaded portion 124 at the distal end of stem 126 of the valve cutter assembly. Thus, differently sized cutter heads with inner threaded female portions could be substituted for cutter head 120, along with a blunt-tipped head to facilitate initial placement of the device. The blunt-tipped head 130, which is illustrated in FIG. 4B, includes a body 132 having a blunt portion 134 and an irrigation port 134, and an internally threaded portion 135.

Figure 4C:
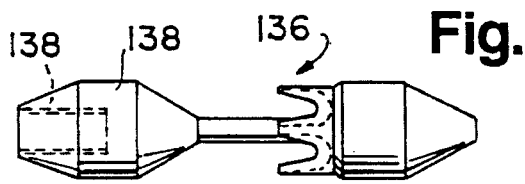

An alternative unitary interchangeable cutter head and leader 136 is illustrated in FIG. 4C. It includes a leader 138 with an inner female threaded portion 138 dimensioned to screw onto the corresponding male threaded portion 140 at the end of catheter 142 (FIG. 4D).

Figure 4B:
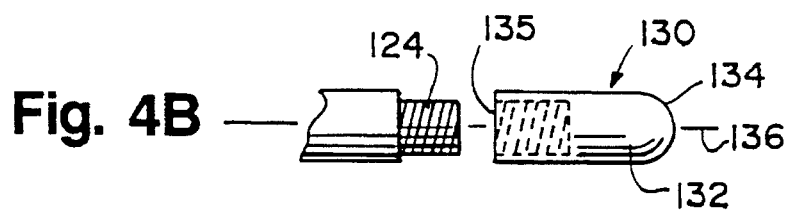
FIG. 4B is an elevation view of a blunt-tipped head used to facilitate placement of the venous valve cutter when interchangeable cutting heads are to be used.
Figure 4D:
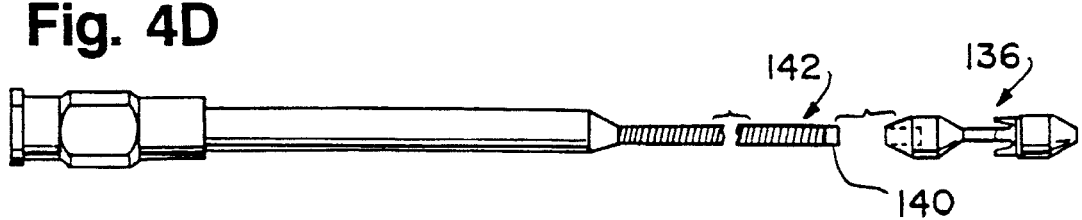

Use of the interchangeable valve cutter heads of FIGS. 4A–4C begins by introducing the valve cutter assembly fitted with the blunt-tipped head 130 through the most proximal end of the vein while heparinized saline is irrigated through the port to dilate the vein prior to advancing the device distally. The distal end of the vein is gently closed with a clamp or between the fingers of an assistant to allow for the dilation of the vein. With the vein distended, the valvulotome is gently advanced allowing it to float distally. When the catheter reaches the open sapheno-femoral junction, (or is passed out through a distal adequate tributary when the distal anastamosis is performed prior to the valve disruption procedure) the blunt tip head is removed and replaced with an appropriately sized valve cutter head. The saphenous vein is again clamped at its open fossa ovalis. The surgeon must choose a cutting head appropriate for the size of the patient's greater saphenous vein.

The valve cutter is then positioned at the most distal aspect of the vein. Fluid is injected through the catheter which distends the lumen and passes back over the cutting head and closes the valve which is now appropriately positioned for cutting. The fluid is injected to present a dilated vessel for the floatation of the device and a functionally closed valve for the cutting head to engage.

The valve cutter is withdrawn thus engaging and cutting the most distal valve. Slow and consistent traction is all that is required. The hydrostatic pressure is maintained and the valve cutter assembly is pulled down engaging and cutting each sequential valve, until all valves have been rendered incompetent within the appropriate range relative to the chosen cutting head. Judgment of the surgeon best determines when the catheter is again passed back through the unclamped distal sapheno-femoral junction where the cutting head is replaced with a larger head.

The procedure is repeated and again judgment determines the appropriately sized cutting head for the vessel's lumen. The appropriately sized valve cutting head will best cut the valves at a given position in the vessel. Preferred cutting head sizes include 1.5 mm, 2.4 mm, 3.0 mm and 4.0 mm. The choice of the particular size is a matter of judgement although it is recommended that a size smaller than the vein be employed. The ability to change cutting heads in this catheter allows the surgeon to appropriately match the heads to the vessel's tapering lumen.

Finally, current devices fitted with fiber optic elements at best permit the surgeon to view the valve distally and do not permit the cutting edge to be viewed as it penetrates the valve because the vessel collapses as the cutter penetrates through the valves. As illustrated in FIG. 9, in the present device the valve can be visualized proximately so that the cutting edge can be observed as it penetrates without the vessel collapsing. In this manner, each and every valve can be observed by the surgeon as the cutter edge penetrates.

Thus, FIG. 9 illustrates an enlarged partial view of an alternative embodiment of the improved venous valve cutter of the present invention in which a fiber optic element is provided for viewing the vessel, the action of the cutting head in rendering the valves incompetent, and for assessing the effectiveness of the cut. In this embodiment, the cutting end 150 of the cutter head is fixed to a leader 152 in which a fiber optic element 154 is mounted. This unique fiber optic mounting permits the surgeon to observe the cutting edge of the cutter head as it penetrates each valve using conventional apparatus (not shown).

It should be understood that various changes and modifications to the preferred embodiments described herein will be apparent to those skilled in the art. Such changes and modifications can be made without departing from the spirit and scope of the present invention and without diminishing its attendant advantages. It is therefore, intended that such changes and modifications be covered by the following claims.

What we claim is:

1. A method of in-situ removal of venous valve leaflets from a saphenous vein having a proximal end and a distal end and a lumen tapering from its distal end to its proximal end comprising:

a) introducing at the proximal end of the vein a valve cutter assembly with a blunt-tipped head and an irrigation channel at its distal tip;

b) introducing fluid through the distal tip of the blunt-tipped head to dilate the vein and, with the vein distended, advancing the valve cutter assembly distally;

c) removing the blunt-tipped head when the assembly reaches the sapheno-femoral junction or an adequate distal tributary of the saphenous vein and replacing it with an appropriately sized valve cutter head also having an irrigation channel at its distal tip and clamping the saphenous vein at its open fossa ovalis or distal to the distal saphenous valve;

d) positioning the valve cutter head at the distal end of the vein, injecting fluid through the channel in the cutter head thereby closing the valve;

e) pulling back on the valve cutter assembly to engage and cut the most distal valve and then maintaining hydrostatic pressure while the valve cutter assembly is pulled down to engage and cut each sequential valve until all valves have been rendered incompetent; and f) repeating steps d) and e) with a plurality of appropriately sized valve cutter heads to match the heads to the vein's tapering lumen.

2. An improved venous valve cutter comprising:

a cutter head having a forward circular cutting edge and means for advancing said cutter head through a vein to render valve leaflets incompetent, said circular cutting edge having a plurality of proximally directed prongs presenting sharp leading edges, said prongs having flat leading edges and being separated by slots similarly presenting sharp cutting edges; and fiber optic means directed distally and positioned proximally to the circular cutting edge for viewing the cutting of the venous valve leaflets as the cutting edge of the valve cutter advances through the vessel and assessing the cut.

3. An improved venous valve cutter comprising:

a cutter head having a forward circular cutting edge and means for advancing said cutter head through a vein to render valve leaflets incompetent, said circular cutting edge having a plurality of proximally directed prongs presenting sharp leading edges, said prongs having flat leading edges and being separated by slots similarly presenting sharp cutting edges;

a leader having a diameter generally equal to that of said cutter head and a stem connecting said cutter head and said leader; and fiber optic means mounted in the leader proximal to the circular cutting edge for viewing the cutting of the venous valve leaflets by the cutting edge as the valve cutter advances through the vein and assessing the cut.

4. An improved venous valve cutter comprising:

a cutter head having a forward circular cutting edge and means for advancing said cutter head through a vein to render valve leaflets incompetent, said circular cutting edge having a plurality of proximally directed prongs presenting sharp leading edges, said prongs having flat leading edges and being separated by slots similarly presenting sharp cutting edges; and fiber optic means mounted in the leader proximal to the circular cutting edge for viewing the cutting of the venous valve leaflets by the cutting edge as the valve cutter advances through the vein and assessing the cut.

5. A method of in-situ removal of venous valve leaflets from a vein having an inner wall comprising:

a) introducing at the proximal end of the vein a valve cutter with a cutter head having a proximal end, a distal tip, and a plurality of proximally directed prongs with sharp edges in which the prongs are separated by slots also having sharp edges, with means for advancing the cutter head through a vein to render valve leaflets incompetent and fiber optic means directed distally and positioned proximally to the circular cutting edge;

b) advancing the cutter head up through the vein from the proximal end to the distal end;

c) reversing the direction of movement of the valve cutter;

d) engaging the leaflets with the cutter head while viewing the cutting of the venous valve leaflets by the cutting edge as the valve cutter advances through the vessel and assessing the cut; and e) rendering successive valves incompetent.

* * * * *

UNITED STATES PATENT AND TRADEMARK OFFICE
CERTIFICATE OF CORRECTION

PATENT NO. : 5,601,580
DATED : February 11, 1997
INVENTOR(S) : Mark C. Goldberg, et al.

It is certified that error appears in the above-indentified patent and that said Letters Patent is hereby corrected as shown below:

On the title page: Item [75]

after "Inventors: Mark C. Goldberg, Boston Mass.; Alexander Poloyko, Morton Grove, Ill." insert -- ; Edward M. Goldberg, Glencoe, Ill.; Lev A. Melinyshyn, Buffalo Grove, Ill. --

Signed and Sealed this

Twenty-second Day of July, 1997

Attest:

BRUCE LEHMAN

*Attesting Officer*　　　*Commissioner of Patents and Trademarks*